(12) United States Patent
Wiesemann

(10) Patent No.: US 9,867,679 B1
(45) Date of Patent: Jan. 16, 2018

(54) DENTAL SHIELD AND METHOD THEREOF

(71) Applicant: Ryan B. Wiesemann, Bowling Green, KY (US)

(72) Inventor: Ryan B. Wiesemann, Bowling Green, KY (US)

(*) Notice: Subject to any disclaimer, the term of this patent is extended or adjusted under 35 U.S.C. 154(b) by 598 days.

(21) Appl. No.: 14/230,615

(22) Filed: Mar. 31, 2014

Related U.S. Application Data

(62) Division of application No. 13/242,097, filed on Sep. 23, 2011, now Pat. No. 8,684,728.

(51) Int. Cl.
 A61C 3/00 (2006.01)
 A61C 7/14 (2006.01)

(52) U.S. Cl.
 CPC .................................. A61C 7/146 (2013.01)

(58) Field of Classification Search
 CPC ...................................... A60C 7/146
 USPC ..... 433/29, 30, 31, 116, 125, 126, 136, 137, 433/140; 128/206.21, 206.22, 206.24, 128/206.25, 206.28, 206.29, 207.11, 856, 128/857–859, 917, 918, 4, 6, 203.12; 95/285
 See application file for complete search history.

(56) References Cited

U.S. PATENT DOCUMENTS

| | | | |
|---|---|---|---|
| 2,762,368 A | 9/1956 | Bloomfield | |
| 3,152,588 A | 10/1964 | Rogowski | |
| 3,772,790 A | 11/1973 | Swan-Gett et al. | |
| 4,323,063 A | 4/1982 | Fisichella | |
| 4,344,758 A | 8/1982 | Wielhouwer et al. | |
| 4,522,594 A | 6/1985 | Stark et al. | |
| 4,626,211 A | 12/1986 | Coston | |
| 4,640,685 A | 2/1987 | Croll | |
| 4,662,842 A | 5/1987 | Croll | |
| 4,701,129 A | 10/1987 | Hazard | |
| 4,701,965 A | 10/1987 | Landis | |
| 4,737,104 A | 4/1988 | Croll | |
| 4,825,878 A | 5/1989 | Kuntz et al. | |
| 4,859,184 A | 8/1989 | Hazard | |
| 4,952,143 A | 8/1990 | Becker et al. | |
| 4,969,473 A | 11/1990 | Bothwell | |
| 4,986,282 A | 1/1991 | Stackhouse et al. | |
| 5,226,815 A | 7/1993 | Bowman | |
| 5,288,231 A | 2/1994 | Kuehn et al. | |
| D347,090 S | 5/1994 | Brunson | |
| 5,341,513 A | 8/1994 | Klein et al. | |
| 5,582,187 A | 12/1996 | Hussey | |
| 5,647,060 A | 7/1997 | Lee | |
| 5,682,879 A | 11/1997 | Bowers | |
| 5,697,780 A * | 12/1997 | Tuneberg | A61C 7/12 206/369 |
| 5,704,349 A | 1/1998 | Hubbard et al. | |
| 5,706,828 A | 1/1998 | Shiota | |

(Continued)

FOREIGN PATENT DOCUMENTS

| | | | | |
|---|---|---|---|---|
| FI | WO 9405175 A1 * | 3/1994 | ............... | A42B 3/28 |
| GB | 2186194 | 8/1987 | | |
| WO | 9405175 | 3/1994 | | |

Primary Examiner — Eduardo C Robert
Assistant Examiner — Mirayda A Aponte
(74) Attorney, Agent, or Firm — Middleton Reutlinger

(57) ABSTRACT

Apparatus related to a dental shield. Light may be filtered or blocked through the dental shield to delay the curing of a light-cured adhesive or cement. The shield has an elevated portion designed to provide clearance sufficient for a bracket as well as a nose relief and breathing passages.

18 Claims, 7 Drawing Sheets

(56) References Cited

U.S. PATENT DOCUMENTS

| | | | |
|---|---|---|---|
| 5,717,993 | A | 2/1998 | Roberts |
| 5,730,599 | A | 3/1998 | Pak |
| 5,732,410 | A | 3/1998 | Machson |
| 5,785,052 | A | 7/1998 | Johnson |
| 5,899,206 | A | 5/1999 | La Chappelle-Reynolds |
| 5,938,435 | A | 8/1999 | Raspino, Jr. |
| 6,079,980 | A | 6/2000 | Durand |
| 6,155,823 | A | 12/2000 | Nagel |
| 6,213,125 | B1 | 4/2001 | Reese et al. |
| 6,216,695 | B1 | 4/2001 | Ruben |
| 6,345,982 | B1 | 2/2002 | Meyer |
| 6,523,179 | B1 | 2/2003 | Zegarelli et al. |
| 6,945,249 | B2 | 9/2005 | Griesbach, III et al. |
| 7,017,577 | B2 | 3/2006 | Matich |
| 7,128,070 | B2 | 10/2006 | Wiener et al. |
| 7,160,111 | B2 | 1/2007 | Baughman |
| 7,273,369 | B2 | 9/2007 | Rosenblood et al. |
| 7,621,746 | B2 | 11/2009 | Baughman |
| 7,802,572 | B2 | 9/2010 | Hahne |
| 8,336,549 | B2 | 12/2012 | Nashed |
| 2003/0213050 | A1 | 11/2003 | Fournier |
| 2006/0154197 | A1* | 7/2006 | Gargiulo ............ A61B 1/24 433/29 |

\* cited by examiner

DENTAL SHIELD AND METHOD THEREOF

CROSS-REFERENCE TO RELATED DOCUMENTS

This divisional application claims priority to and benefit from, currently pending, U.S. patent application Ser. No. 13/242,097, titled "Dental Shield" and having filing date Sep. 23, 2011, all of which is incorporated by reference herein.

TECHNICAL FIELD

Present embodiments pertain to a dental shield. More specifically, present embodiments pertain to a dental shield which inhibits curing of light curable fixatives used with brackets for dental or orthodontic braces, or other uses.

BACKGROUND

It is common in the field of orthodontics to secure orthodontic brackets in place on a patient's tooth using light-cured adhesive or cement. The light-cured adhesive or cement used often cures when exposed to ultra-violet light. Some states may require an orthodontist to place a bracket before the cement is cured, but even in states with no such requirement orthodontists may still wish to place the brackets themselves. At the same time, the trend in modern orthodontics has been for orthodontists to become more efficient, that is, to see more patients in less time. However, the common practice of an orthodontist placing brackets often leads to a situation where an orthodontist becomes a bottleneck in the treatment of patients and thus this common practice may decrease the efficiency of an orthodontic practice. To help increase efficiency, it may often be desirable for an orthodontic assistant to place orthodontic brackets on patients' teeth using light-cured adhesives or cement but to also delay the light-curing of the adhesive or cement. This delay of curing may allow an orthodontist to inspect the brackets and the placement of the brackets without significantly slowing the treatment of patients.

It would also be desirable to delay curing of fixatives used with application of dental implants in order to allow a dentist to properly adjust the implant prior to curing of the fixative.

It would be desirable to overcome these and other deficiencies in the application of orthodontic braces, implants or other applications utilizing light curable fixatives.

SUMMARY

In some embodiments of an orthodontic shield, there may be provided, in any combination, some or all of the following: a base, an upper member, a nose relief, and one or more breathing passages. The base may be shaped to rest on a person's face or on cheek retractors in such a way as to cover the person's mouth. The base may have a substantially planar top surface and a substantially planar bottom surface. The top surface and the bottom surface of the base may be substantially parallel, although the top surface and the bottom surface may alternatively be formed in other shapes.

In some embodiments, the upper member may have a top portion having a top face and a bottom face. The top face and the bottom face of the top portion of the upper member may be substantially planar. The upper member may have at least one top portion, a left side support portion, a right side support portion, and a front side support portion. In an alternative embodiment, the upper member may be substantially dome-shaped, where the top face and the bottom face of the upper member are substantially concentric domes. The upper member may be elevated from the base to provide sufficient clearance, between the bottom face of the upper member and a person's tooth, for an orthodontic bracket or other orthodontic device or other implement such as an implant veneer. The upper member may be substantially translucent and may also have light-filtering characteristics, including but not limited to, ultra-violet light filtering characteristics. Alternatively, the upper member and/or the entire shield may be opaque and not allow any light passage therethrough.

In some embodiments, the base may have a mouth and nose relief wherein there is an opening that leaves a person's mouth and nose substantially uncovered by the base. The mouth relief of the base may be substantially covered by the upper member, with the upper member at an elevation sufficient to provide clearance for an orthodontic bracket or other orthodontic device. The upper member may have a nose relief wherein there is an opening that leaves a person's nose substantially uncovered by the orthodontic shield. The top portion of the upper member may have a shape similar to, but slightly larger than, the mouth relief of the base member. In this way, top portion of the upper member may slightly overlap the base on some or all sides of the mouth relief so that support portions of the upper member may attach to the base, supporting the top portion of the upper member at an elevation thereto.

In some embodiments, one or more openings may be located in the upper member adjacent to the support portions. The openings may be substantially perpendicular to the top face of the base and/or the bottom face of the upper member. The openings may be substantially parallel to the faces and base and may be offset vertically and/or horizontally from one another. The openings may extend sufficiently far through the upper member so as to create a breathing passage. The opening(s) may allow airflow so that the openings may be used as a breathing passage(s) for a person wearing the dental shield. In this way, the dental shield may cover a patient's mouth while still allowing the patient to breathe through his or her mouth because inhaled and exhaled air may pass through the breathing passage(s). Thus, with the aforementioned nose relief and the breathing passage(s), a patient may breathe substantially unimpeded, whether through mouth or nose, while wearing the dental shield. At the same time, with the breathing passage(s) arranged substantially perpendicular to the path of external light rays, light may not pass through to the patient's mouth without passing through the light filtering or blocking upper member.

In an alternative embodiment, there may be a base, a first upper member, a second upper member, a nose relief, and one or more breathing passages. The first upper member may be substantially the same as the aforementioned upper member, except that the first upper member may, in the alternative embodiment, have one or more apertures substantially parallel to the bottom and/or top face of the first upper member. A second upper member may be elevated relative to the first upper member so as to create a cavity between the first upper member and the second upper member. The second upper member may be elevated by one or more additional support portions extending at least from a top side of the first upper member to a bottom side of the second upper member. The second upper member may have one or more apertures substantially offset from the aperture(s) of the first upper member. The aperture(s) of the first upper member and the aperture(s) of the second upper member may be arranged in such a way that no aperture of the first upper member overlaps any aperture of the second upper member, or vice versa. The first upper member and/or the second upper member may be at least semi-translucent and the first upper member and/or the second upper member may have light-filtering characteristics. Thus, air may flow through the first and second upper members, via the cavity between the first and second upper members, substantially perpendicular to the first and second upper members, but light may not pass through to the patient's mouth without passing through the first and/or second upper members.

In some embodiments, the base may be made of a material that is at least semi-pliable. The bottom surface of the base member may have a sufficiently high coefficient of friction when resting on cheek retractors or a person's face to prevent the base member from sliding off of the cheek retractors or person's face when the person is in a reclined position. The bottom surface may also have a sufficiently high coefficient of friction when resting on a person's face or cheek retractors to prevent the base member from sliding when the person turns their head, within a certain range, in any direction. The base may be at least semi-pliable so that it may, at least somewhat, conform to the contours of a human face. The base may have a thickness sufficient to provide durability and a weight sufficient to, as a non-limiting example, prevent the base from sliding or being blown by ambient breeze off of a person's face or the cheek retractors. In such a way, the device may be hands-free in that neither the patient, dental assistant nor the dental professional needs to hold the shield in place. The upper member or, in the case of an alternative embodiment an upper member formed of at least a first portion and a second portion, may be made of a translucent material having light filtering characteristics. These upper members may be semi-pliable or rigid, and they may cover a patient's mouth. In this way, the upper member(s) may filter substantially all light that reaches a patient's mouth when the patient is wearing the dental shield. It may be that the orthodontic shield is constructed of one type of material. If the dental shield is constructed of one material, the material may be semi-pliable, translucent, opaque and light filtering.

According to some embodiments, a dental shield, comprises a base and an upper member, wherein at least a portion of one of the base and the upper member is formed of at least a semi-translucent material having ultra-violet light filtering characteristics, one of the base and the upper member having a nose relief, the upper member being elevated from the base to provide a clearance from at least one orthodontic bracket on a patient's tooth, the base having a top face and an aperture large enough to allow at least a portion of a person's mouth to be substantially uncovered by the base, the upper member having a bottom face wherein the bottom face of the upper member is at least large enough to substantially cover the aperture of the base, the bottom face of the upper member being elevated from the top face of the base by at least one support, at least one air flow aperture allowing air to flow substantially parallel to at least one of the top face of the base and the upper member. The dental shield wherein the base is substantially planar. The dental shield wherein the upper member is substantially planar. The dental shield wherein the upper member is substantially convex. The dental shield wherein the translucent material is substantially rubber. The dental shield wherein at least a portion of the body is at least semi-pliable. The dental shield wherein the at least one air flow aperture is substantially perpendicular to at least one of the top face and the base, and the bottom face of the upper member. The dental shield wherein the at least one air flow aperture is a first aperture in the upper member offset a distance from a second aperture in the base.

According to some embodiments, a dental shield comprises a base and an upper member, wherein at least one of the base and the upper member is at least partially formed of a translucent material having ultra-violet light filtering characteristics, wherein at least a portion of the dental shield is at least semi-pliable, the base having a cut-away portion that is positionable over a person's mouth, the upper member having a base, a first portion and a second portion, the upper member being elevated from the base to provide a clearance between the body and at least one orthodontic bracket on a patient's tooth, the base having a top face and a mouth relief, the first portion being elevated from the top face of the base by at least one support portion, the second portion spaced above the base, at least one aperture located in one of the dental shield inhibiting ingress of external light through the dental shield. The dental shield wherein the base is substantially planar. The dental shield wherein the first portion is substantially planar. The dental shield wherein the first portion is substantially convex. The dental shield wherein the second portion is substantially planar. The dental shield wherein the second portion is substantially convex. The dental shield wherein the first portion and the second portion being parallel. The dental shield wherein the at least one aperture is a first aperture and a second aperture offset from the first aperture. The dental shield wherein the second upper member is substantially convex. The dental shield wherein the translucent material is substantially rubber.

According to one embodiment, a method of inhibiting light from curing a dental fixative comprises the steps of placing at least one dental implement which utilizes a curable fixative in a patient's mouth, positioning a dental shield over the patient's mouth, limiting light exposure to the fixative with the dental shield and, removing the dental shield when a dental professional has approved positioning of the implement.

Optionally, the method further comprises inserting a cheek refractor. The positioning of the dental shield may be on the cheek refractor. Alternatively, the positioning may be directly on the patient's face. The dental implement may be an orthodontic bracket. The curable fixative may be reactive to ultraviolet light. The method provides for patient breathing through the dental shield. The dental shield provides clearance for the dental implement. The method may further comprise adjustment of the dental implement before the curing begins. The method further comprises removing the dental shield to begin curing the curable fixative.

According to another embodiment, a method of inhibiting light from curing a dental fixative comprises applying the fixative to one of a dental bracket and a tooth, applying the dental bracket to the tooth, positioning a dental shield having breathing apertures over a patient's mouth with the dental bracket, delaying curing of the dental fixative, reviewing positioning of the dental bracket, and, removing the dental shield upon approval of positioning of the dental bracket.

Optionally, the method of inhibiting light from curing a dental fixative wherein the positioning of the dental shield being directly on the patient's mouth. The positioning of the dental shield being on a cheek refractor. The method provides a clearance between the dental bracket and the dental shield. The method further comprising adjusting the dental bracket after the reviewing. The delaying inhibits light from curing the dental fixative.

According to still a further embodiment, a method inhibiting light from curing a dental fixative with a dental shield having a base and an upper member which filter ultraviolet light and provide clearance for a dental bracket in a patient's mouth comprises applying the dental fixative to the dental bracket, positioning the dental bracket on a tooth of the patient's mouth, placing the dental shield over the patient's mouth, inhibiting light exposure to the dental fixative so that a dental professional can review positioning of the dental bracket; and removing the dental shield following the review of the positioning.

Optionally, the method further comprises adjusting the dental bracket.

BRIEF DESCRIPTION OF THE ILLUSTRATIONS

The above-mentioned and other features and advantages of this invention, and the manner of attaining them, will become more apparent and the invention will be better understood by reference to the following description of embodiments of the invention taken in conjunction with the accompanying drawings, wherein.

DETAILED DESCRIPTION

Figure 1:
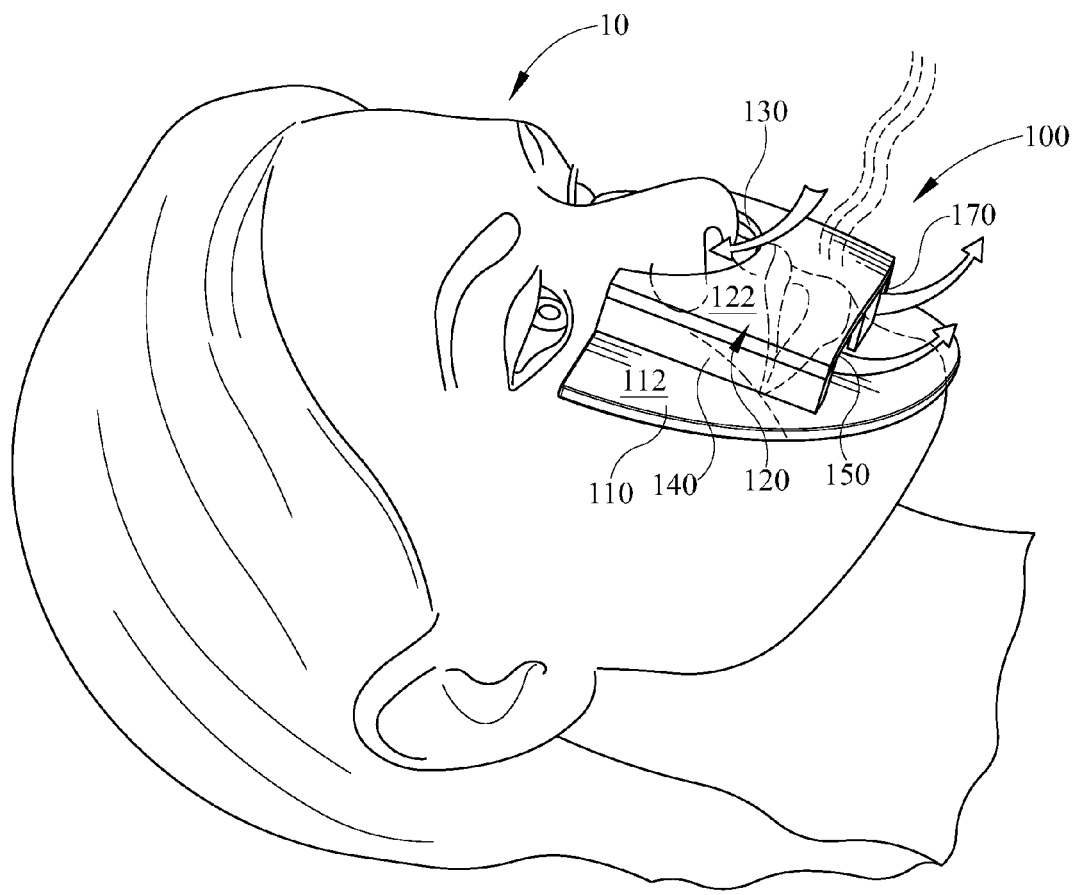
FIG. 1 is an illustration of an embodiment of the dental shield in use on a patient's face.

It is to be understood that the invention is not limited in its application to the details of construction and the arrangement of components set forth in the following description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. The term dental implement should be understood to include any bracket, implement, implant or other dental structure which utilizes a light curable fixative.

A dental shield is shown in the various FIGS. 1-9. The dental shield utilizes an at least semi-pliable material which has ultraviolet light filtering characteristics so as to limit curing of light curable fixatives, including but not limited to epoxy, cements, composites, and the like, typically used in positioning orthodontic brackets of dental braces, implant, implements or other structures. The description of the dental shield however should not be construed as limited to orthodontic uses. Instead the term dental should be considered more broad so as to include orthodontic as well as other uses, such as for example dental implants. The light limiting characteristics should be understood to include light blocking materials as well. The dental shield has a nose relief to allow breathing and a mouth relief to elevate the shield above the bracket and not interfere therewith. The shield also inhibits curing of epoxy until the dental professional approves of positioning of the one or more brackets on the teeth, implants in a mouth or other uses. This apparatus relieves the bottleneck which may typically occur during installation of braces and aids to increase efficiency of the dental professional, for example.

Embodiments of the invention may further be understood with reference to FIG. 1, which illustrates a dental shield 100 in use on a patient's face 10. FIG. 1 illustrates a translucent and light filtering shield 100 as it might be positioned while in use. This figure also illustrates the arrangement of a nose relief 130 around a patient's nose as well as breathing passages 150, 170. A base 110 comes in contact with a patient's face. In this figure, the base 110 is illustrated as being a substantially planar semi-circle with a rectangular mouth and nose relief to accommodate a patient's mouth. It is understood that the base 110 and reliefs could also be a number of other shapes, such as a rectangle, square, triangle, or other shape. Base 110 is depicted in FIG. 1 as having a top face 112 that is substantially planar but may be other geometries, such as convex for example. An upper member 120 is illustrated extending from the base 110 and is parallel thereto, forming the dental shield 100. Upper member 120 is illustrated with a substantially planar top face 122. While upper member 120 is illustrated as being generally rectangular in shape with nose relief 130 and breathing passages 150, 170, it is understood that upper member 120 could also be a number of other shapes, such as convex, dome, a pyramid, or other prisms or shapes.

Upper member 120 is illustrated with a left breathing passage 150 and a right breathing passage 170. FIG. 1 illustrates breathing passages 150, 170 on the front side of the upper member 120. However, it is understood that one breathing passage may be used, or any number of breathing passages could be used, and FIG. 1 merely is illustrative. Likewise, the upper member 120 may have one or more breathing passages on the left side (FIG. 2) and/or the right side additional to, or in lieu of, one or more breathing passages on the front side of the upper member 120. FIG. 1 also shows a nose relief 130 for accommodating a patient's nose. While FIG. 1 illustrates the nose relief 130 substantially as a semi-circle, it is understood that the nose relief 130 could be a number of other shapes as well, such as a square, a rectangle, a triangle, or other shape.

The shield 100 may be formed of various materials which filter ultraviolet light in various manners. The term filter should be understood to mean partially or completely block light. Additionally, the material may block more than just UV light. For example, the material may be opaque or solid so as to block all light from entering the patients mouth. The present exemplary shield 100 is formed of urethane rubber. This at least semi-pliable material inhibits the ultraviolet light from curing the epoxy. Other materials which may be used include silicone, plastic, acrylic, composites, paper and the like.

Figure 2:
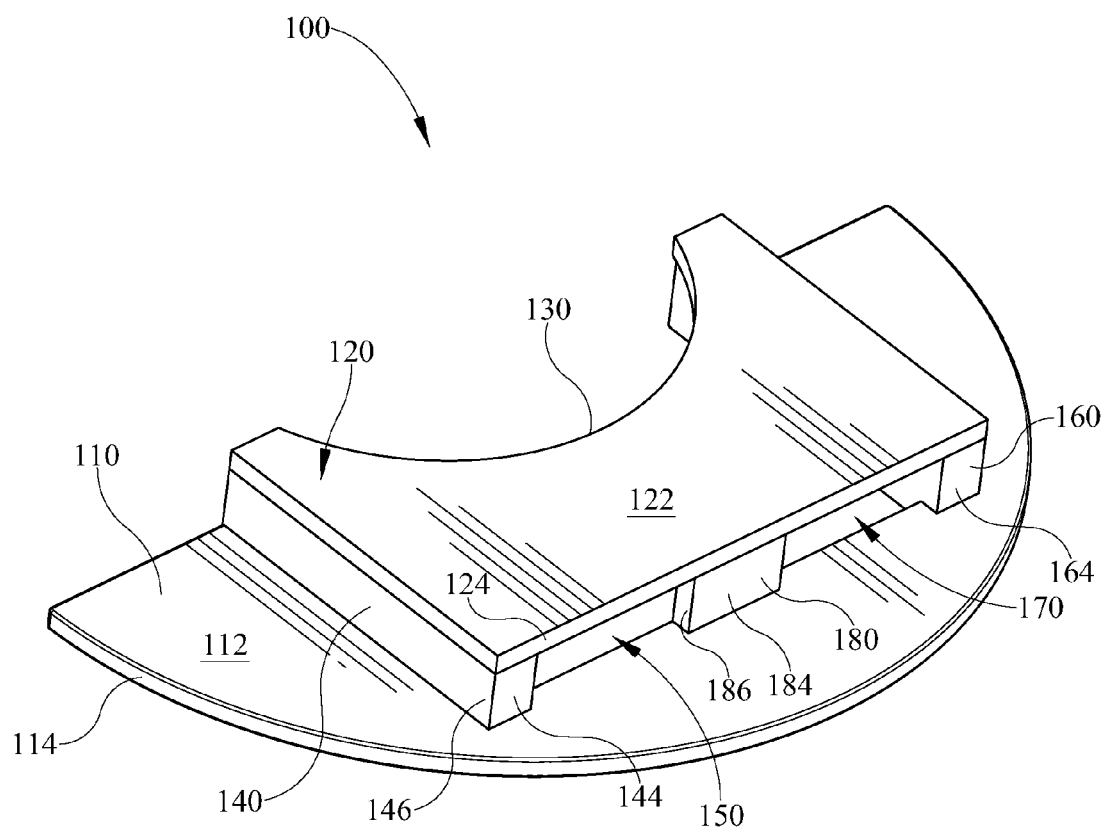
FIG. 2 is an illustration of the dental shield of FIG. 1 standing alone.

FIG. 2 is a perspective view of an embodiment of the shield 100. This figure illustrates a base 110 and an upper member 120. The exemplary base 110 in this figure has a substantially planar top surface 112 and is substantially semi-circular in shape. It is understood that a number of other shapes could be used for the base as well, such as a square, a rectangle, a triangle, or another shapes. The base is also illustrated with a front face 114. The upper member 120 is illustrated with a substantially planar top face 122 and a substantially planar front face 124. It is understood that the upper member 120 could be a number of other shapes as well, such as a dome, a pyramid, another type of prism, or another shape. In this illustration, the front face 124 of upper member 120 is substantially perpendicular to the top face 122 of upper member 120. It is understood however, that the front face 124 may be angled relative to the top face 122 at an acute angle or at an obtuse angle or may be curved. FIG. 2 shows a nose relief 130 in the upper member 120. Nose relief 130 is shown as substantially a semi-circle, although it is understood that nose relief 130 could be a number of other shapes as well, such as a square, a rectangle, a triangle, or another shape. FIG. 2 also shows a left side support portion 140, a right side support portion 160, and a front side support portion 180. It is understood that a number of different arrangements of support portions may be used to elevate the upper member 120 from the base 110. FIG. 2 merely shows an example of one arrangement of support portions 140, 160, 180 that may achieve the relative elevation of the upper member 120 to the base member 110.

While support portions 140, 160, 180 are shown in FIG. 2 as being substantially rectangular prisms, other shapes could also be used for the support portions, including, but not limited to, cylinders, rods, angular members, square prisms, or other shapes. The support portions 140, 160, 180 may be integral or may be formed separately and later combined. Similarly, the base 110 and upper member 120 may likewise be formed separately from or may be formed integrally with upper member 120. Further, while FIG. 2 shows one left side support portion 140, one right side support portion 160, and one front side support portion 180, it is understood that more than one support portion per side may be used. It is also understood that using additional support portions, spaced apart from each other, would add additional breathing passages similar to the left side breathing passage 150 and the right side breathing passage 170 shown in FIG. 2. This figure illustrates breathing passages 150, 170 as an opening substantially perpendicular to the top face 112 of base 110 and/or the top face 122 of the upper member 120, wherein the opening extends through the shield in a direction substantially parallel to the top face 112 of base 110 and/or the top face 122 of the upper member 120. It is understood that less than two breathing passages may be used, or more than two breathing passages may be used. It is further understood that breathing passages may also be located on the left side and/or the right side of the upper member, or located on the left side and/or the right side instead of being located on the front side. In any alternative though, ultraviolet light should be limited from direct contact with the patient's teeth having the epoxy.

FIG. 2 also illustrates an outside face 146 of left side support portion 140, a front face 144 of left side support portion 140, a front face 184 of front side support portion 180, a left side face 186 of front side support portion 180, and a front face 164 of right side support portion 160. Faces 146, 144, 186, 184, 164 are shown as being substantially planar, substantially flush with upper member 122, and substantially perpendicular to top face 122 of upper member 120. It is understood that faces 146, 144, 186, 184, 164 need not be planar, they need not be flush with upper member 120, and they could be angled other than 90 degrees with respect to top face 122 or may be curvilinear. FIG. 2 is merely an illustration of an embodiment.

Figure 3:
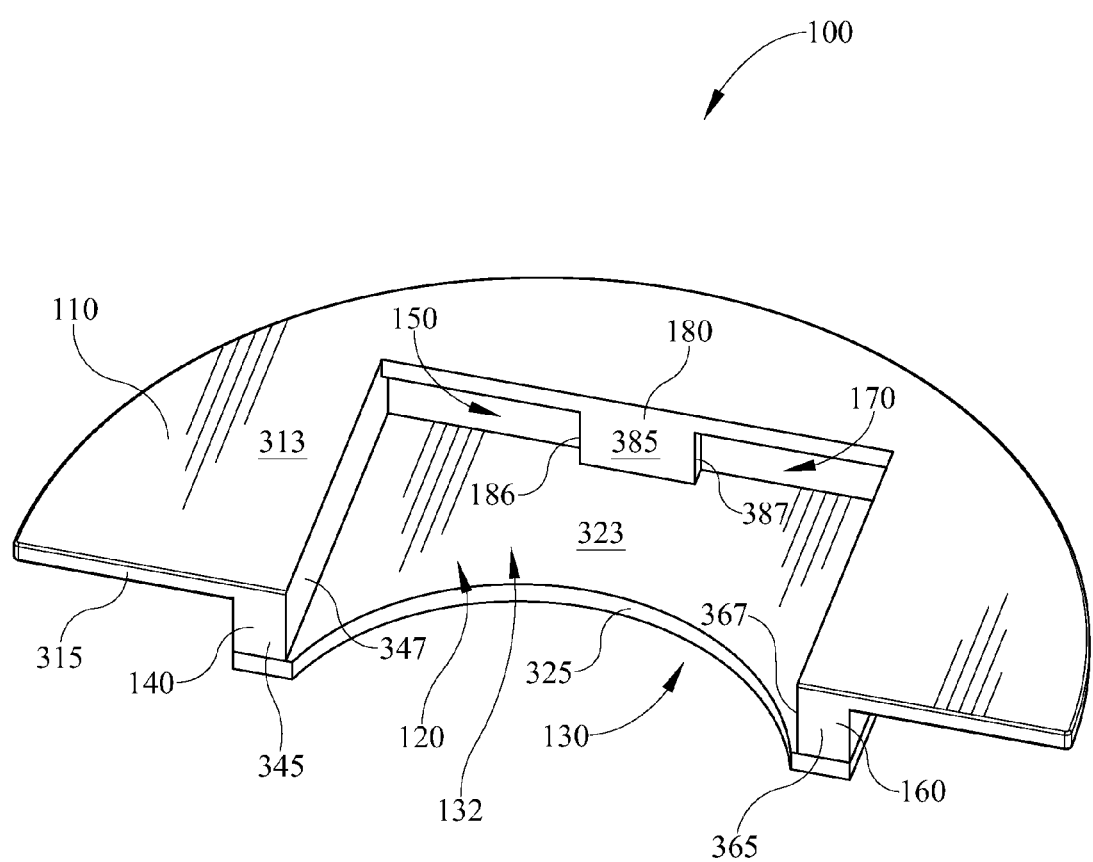
FIG. 3 is an illustration of a perspective view of the bottom of the dental shield.

FIG. 3 is an illustration of a perspective view from the bottom side of an embodiment of the dental or dental shield 100. This figure shows the base 110 having a bottom face 313. Bottom face 313 of base 110 may have a coefficient of friction sufficient to prevent the bottom face 313 from slipping when the shield 100 is in use on a patient's face. The shield 100 further comprises a back face 315 of base 110. Upper member 120 has a bottom face 323 and a back face 325 that at least partially shapes the nose relief 130. A left side support portion 140 has an inside face 347 and a back face 345. A right side support portion 160 has an inside face 367 and a back face 365. Front side support portion 180 is shown having an inside face 385, a left face 186 and a right face 387. Faces 347, 345, 367, 365, 385, 186, 387 are shown as being substantially planar, substantially flush with upper member 120, and substantially perpendicular to top face 122 of upper member 120. It is understood that faces 347, 345, 367, 365, 385, 186, 387 need not be planar, they need not be flush with upper member 120, and they could be angled other than 90 degrees with respect to the bottom face 313 of base 110 and/or the bottom face 323 of upper member 120. FIG. 3 is merely an illustration of an embodiment.

FIG. 3 depicts a mouth relief 132 formed by the cut-away portion of base 110 and the spaced upper member 120. The aperture or mouth relief 132 provides clearance for the patient's mouth and more specifically clearance for the orthodontic bracket placed on the patient's tooth before curing of the epoxy. Thus a technician can place the bracket and wait for the orthodontist to approve or adjust the positioning before the shield 100 is removed and the curing begins to occur.

Figure 4:
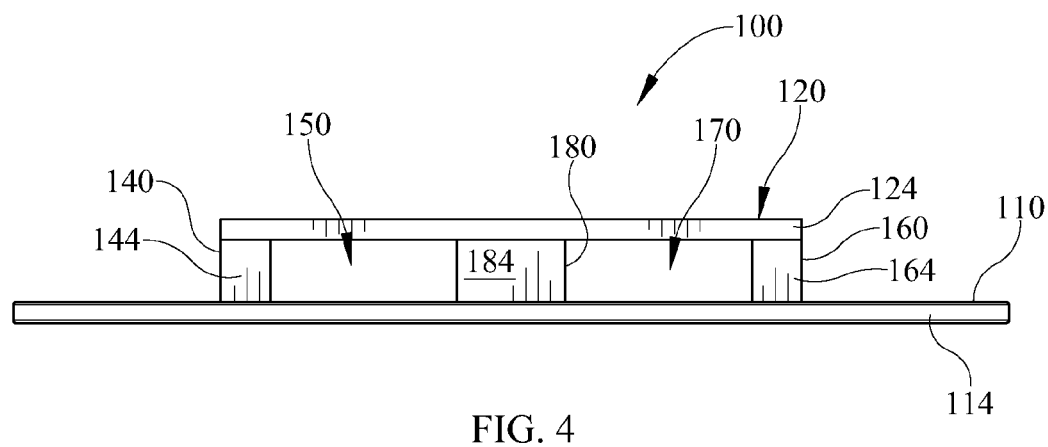
FIG. 4 is an illustration of a front view of the dental shield.

FIG. 4 is an illustration of a front view of an embodiment of the dental shield 100. This figure shows the front face 114 of base 110. It also shows the front face 124 of upper member 120. FIG. 4 shows the front face 144 of left side support portion 140, the front face 164 of right side support portion 160, and the front face 184 of front side support portion 180. This figure also shows left side breathing passage 150 and right side breathing passage 170. While this figure illustrates breathing passages 150, 170 as substantially rectangular, it is understood that the breathing passages 150, 170 could be oval, circular, square, triangular, or one of many other shapes. It is further understood that there may only be one breathing passage, or there may be more than two breathing passages, and that the breathing passage(s) could be located on the left side, right side, and/or front side of the upper member 120.

Figure 5:
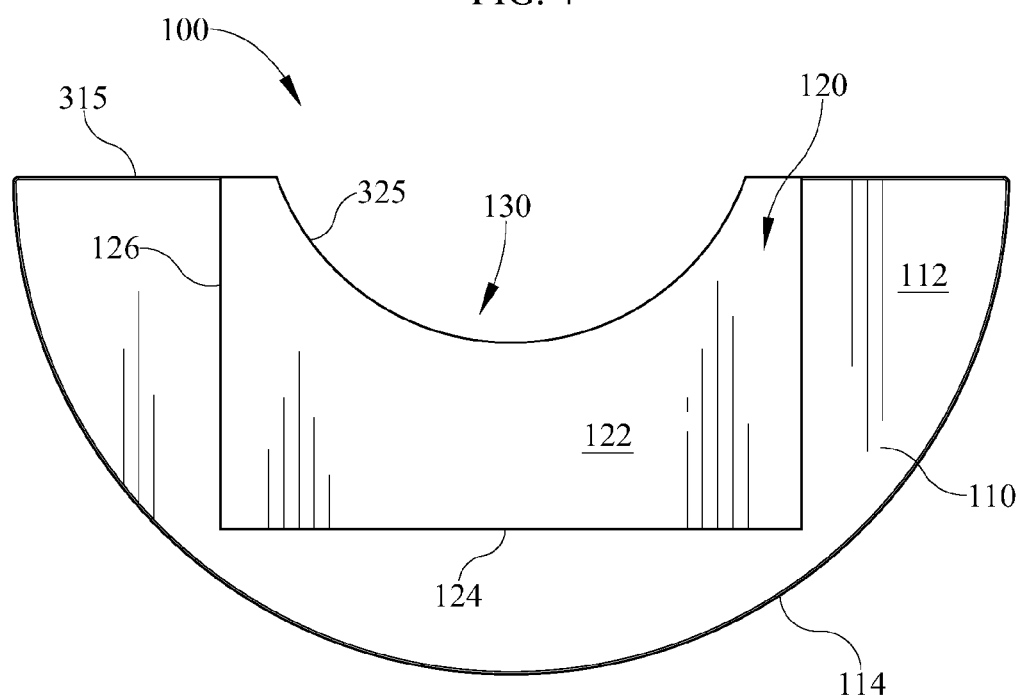
FIG. 5 is an illustration of a top view of the dental shield.

FIG. 5 is an illustration of a top view of an embodiment of the shield 100. This figure illustrates the top face 112, the front face 114, and the back face 315 of base 110. It is understood that the base 110 could have a shape, other than a semi-circle as illustrated in FIG. 5, in which front face 114 may not extend as far around the base, there also may be more than one front face 114. It is also understood that, depending on the shape of the base 110, front face 114 may extend further than is illustrated. FIG. 5 further illustrates the top face 122, the front face 124, the left side face 126, and the back face 325 of upper member 120. FIG. 5 also illustrates the nose relief 130.

Figure 6:
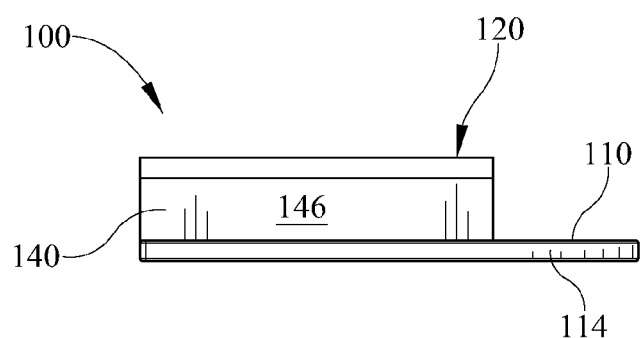
FIG. 6 is an illustration of a left side view of the dental shield.

FIG. 6 is an illustration of a left side view of an embodiment of the shield 100. This figure illustrates the front face 114 of base 110. FIG. 6 illustrates upper member 120 and also the outside face 146 of left side support portion 140.

Figure 7:
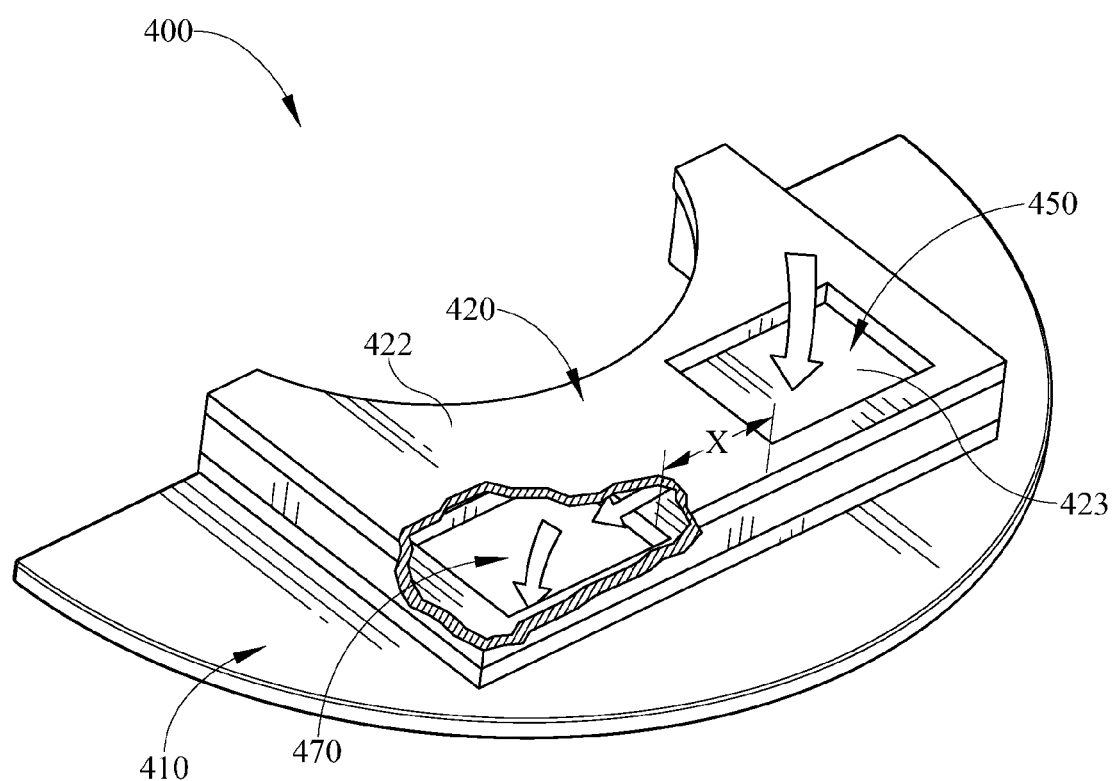
FIG. 7 is an illustration of an alternative embodiment having an alternate airflow path.

Referring now to FIG. 7, an alternative embodiment of a shield 400 is depicted having a base 410 and an upper member having a first portion 422 or second portion 423. The second portion 423 is disposed between the first portion 422 and the base 410. The upper portion 420 includes and air flow aperture 450 which is offset from the lower aperture 470. The offset is represented by a distance "X" in the figure. The offset provides that light is inhibited from traveling in a straight path from the upper aperture 450 through the lower aperture 470 and reaching the epoxy on the patients' teeth. Also this allows airflow to and from the patient's mouth, between the first portion 422 and the second portion 423 as indicated by the airflow arrows shown.

Figure 8:
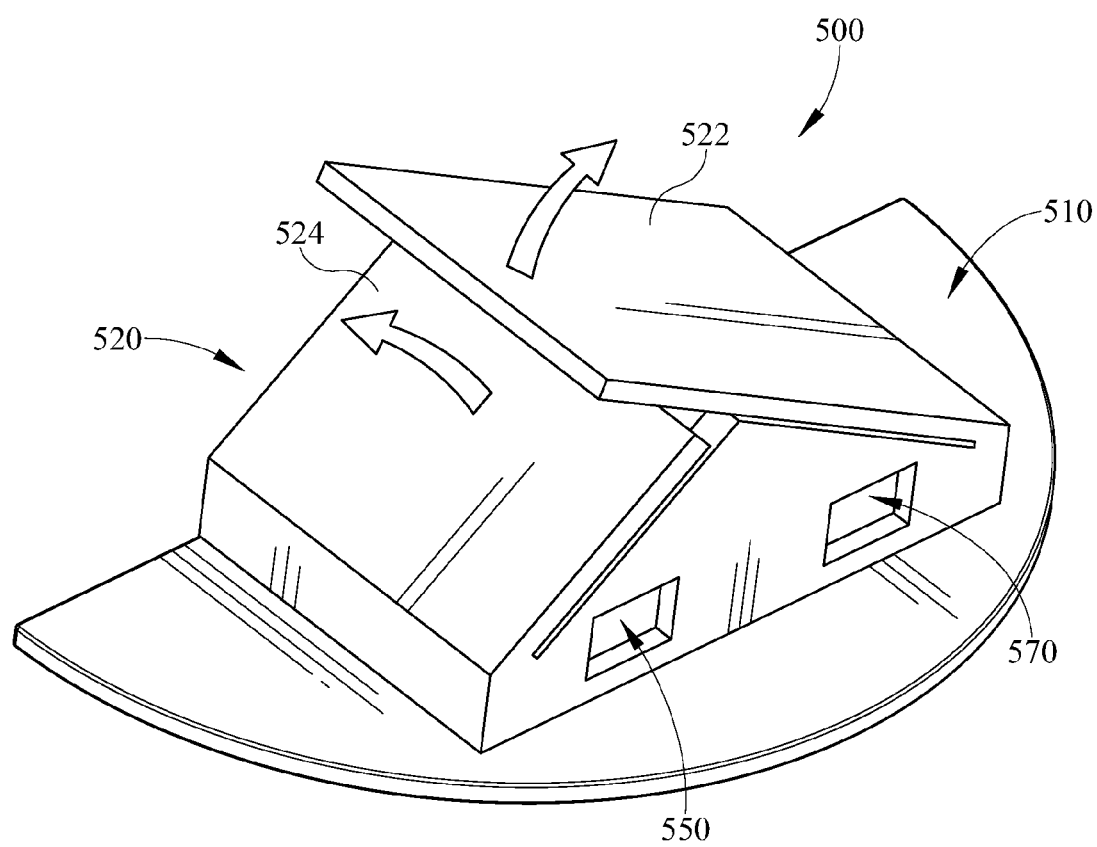
FIG. 8 is an illustration of a further alternative dental shield.

Referring now to FIG. 8, a further alternative embodiment of a light filtering or blocking dental shield 500 is shown. The shield 500 may be formed of a single unitary piece or two or more pieces and is formed of an at least semi-pliable material which may be at least semi-translucent or may be opaque to limit UV light or all light. The shield 500 includes a base 510 and an upper member 520 which may be formed unitarily or may be formed of two pieces, first and second portions, which are joined or may be separable from one another. Toward an upper end of the shield 500 are structures forming tent shaped coverings or portions 522, 524, although other shapes may be used. The coverings or portions 522, 524 may be formed to pivot open, like doors or may be removed entirely if the shield 500 is formed in two or more pieces. The coverings 522, 524 allow the dental professional to view, access and position or re-position dental implants for example before the fixative used to adhere the fixative cures. The dental shield 500 may be, as with the previous embodiments, fully light blocking or may be semi-translucent and/or limiting only UV light, or some function in between. The shield 500 may also have breathing apertures or passages 550, 570 in any of the manners previously described so that light is limited from accessing the teeth below the shield 500. The desired function should be understood as delaying or inhibiting curing of a fixative used with orthodontic braces, implants or veneers.

Figure 9:
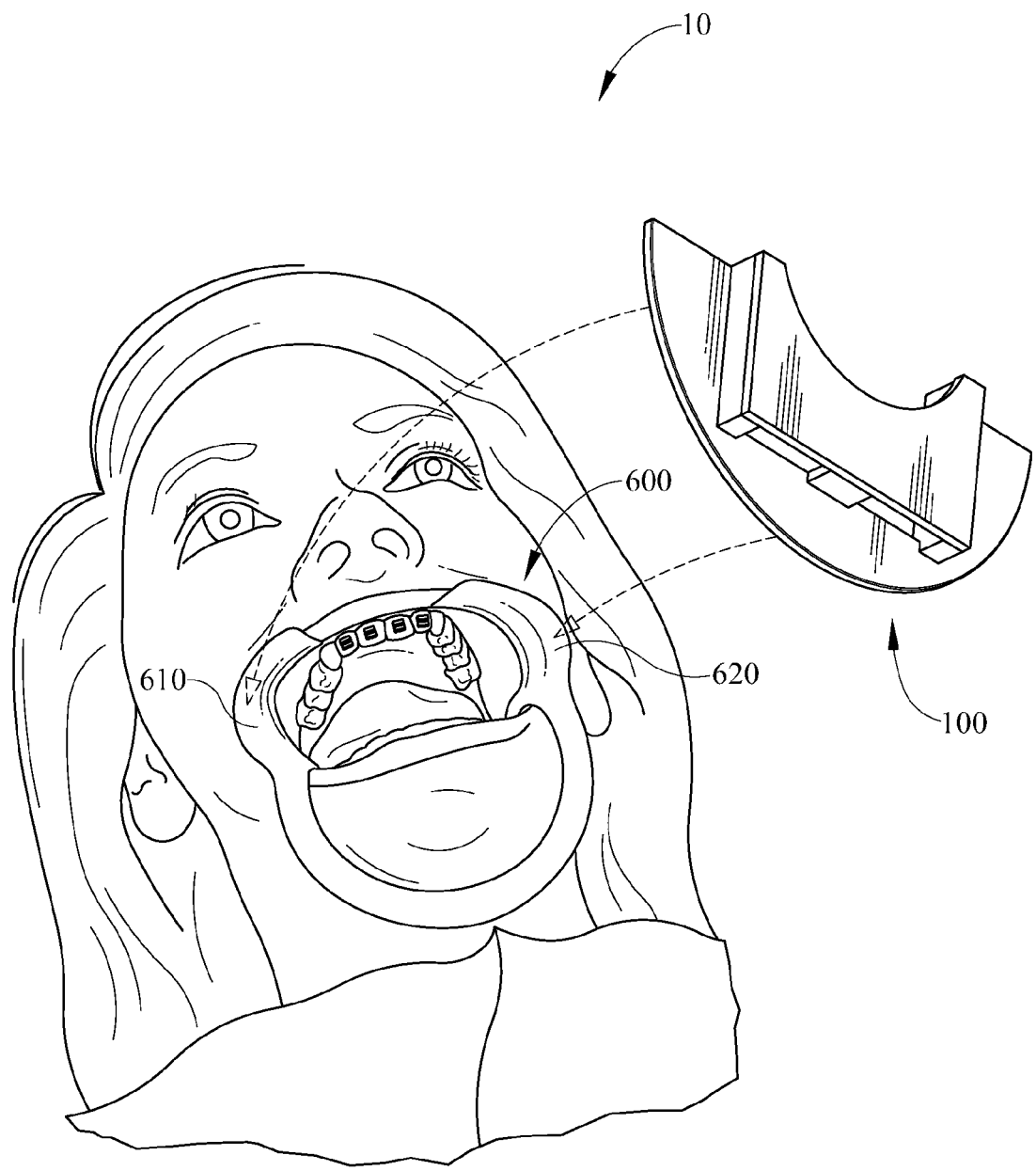
FIG. 9 is a perspective view of a patient with the dental shield exploded from the cheek retractors.

Referring now to FIG. 9 is a perspective view of a user 10 is shown. The user or patient 10 is positioned in a dental chair from the dental professional's perspective and has a cheek retractor 600 inserted into her mouth which allows optimal viewing of the patient's teeth by the dental professional. The cheek retractor 600 may come in various forms, one of which is shown but should not be considered limiting. The exemplary retractor has a first support surface 610 and an opposed second support surface 620. The shield support surfaces 610, 620 provide a surface upon which any of the dental shields described herein previously may be positioned for use. The dental shield is exploded from the cheek retractors 600 and broken line arrows indicate positioning of the shield on the retractors 600.

For example, with the cheek retractor 600 inserted, a technician could first apply a plurality of dental brackets or other implement utilizing a light curable fixative such as cement or epoxy or other known fixative to the patient's teeth. Prior to the curing of the epoxy or cement fixative and, in order to delay such curing, the technician would place the shield on the support surfaces of the cheek retractor 600. It should be understood that the support surface can be any surface of the cheek retractor, the surfaces 610, 620 being merely exemplary. Further, it should be understood that the exemplary dental shields may be utilized without such retractor 600. In either event with the dental shield positioned on the cheek retractor 600, the curing of the fixative is delayed until the dental professional can remove the shield and review the placement of the brackets on the patient's teeth. Once the bracket positioning is approved or adjusted, the dental shield is removed and the curing of the fixative continues.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the invent of embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms. The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

"Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

I claim:

1. A method of inhibiting light from curing a dental fixative, comprising the steps of:
    placing at least one dental implement which utilizes a curable fixative in a patient's mouth;
    positioning a dental shield over the patient's mouth, said shield filtering light and having a raised relief extending from a base, said relief having at least one breathing passage requiring a directional change of air along the breathing passage;
    limiting light exposure to said fixative with said breathing passage of said dental shield; and,
    removing said dental shield when a dental professional has approved positioning of said implement.

2. The method of inhibiting light from curing a dental fixative of claim 1, further comprising inserting a cheek retractor.

3. The method of inhibiting light from curing a dental fixative of claim 2, said positioning said dental shield being on said cheek retractor.

4. The method of inhibiting light from curing a dental fixative of claim 1, said positioning being directly on said patient's face.

5. The method of inhibiting light from curing a dental fixative of claim 1, said dental implement being an orthodontic bracket.

6. The method of inhibiting light from curing a dental fixative of claim 1, said curable fixative being reactive to ultraviolet light.

7. The method of inhibiting light from curing a dental fixative of claim 1, said patient breathing through said dental shield.

8. The method of inhibiting light from curing a dental fixative of claim 1, said dental shield providing clearance for said dental implement.

9. The method of inhibiting light from curing a dental fixative of claim 1, adjusting said dental implement before said curing begins.

10. The method of inhibiting light from curing a dental fixative of claim 1, removing said dental shield to begin curing said curable fixative.

11. A method of inhibiting light from curing a dental fixative, comprising:
    applying said fixative to one of a dental bracket and a tooth;
    applying said dental bracket to said tooth;
    positioning a dental shield having a raised relief extending from a base and breathing apertures in said raised area over a patient's mouth with said dental bracket, said dental shield filtering light and said breathing apertures inhibiting light from traveling in a straight path from said patient's mouth through said dental shield;
    delaying curing of said dental fixative;
    reviewing positioning of said dental bracket; and,
    removing said dental shield upon approval of positioning of said dental bracket.

12. The method of inhibiting light from curing a dental fixative of claim 11, said positioning said dental shield being directly on said patient's mouth.

13. The method of inhibiting light from curing a dental fixative of claim 11, said positioning said dental shield being on a cheek refractor.

14. The method of inhibiting light from curing a dental fixative of claim 11, providing a clearance between said dental bracket and said dental shield.

15. The method of inhibiting light from curing a dental fixative of claim 11 further comprising adjusting said dental bracket after said reviewing.

16. The method of inhibiting light from curing a dental fixative of claim 11, said delaying inhibiting light from curing said dental fixative.

17. A method of inhibiting light from curing a dental fixative with a dental shield having a base and an upper member which filter ultraviolet light and provide clearance for a dental bracket in a patient's mouth, comprising:
    applying said dental fixative to said dental bracket;
    positioning said dental bracket on a tooth of said patient's mouth;
    placing said dental shield over said patient's mouth, said dental shield filtering light and having a raised relief extending from a base at least one breathing aperture which inhibits light from passing linearly through said breathing aperture into said patient's mouth;
    inhibiting light exposure to said dental fixative so that a dental professional can review positioning of said dental bracket; and
    removing said dental shield following said review of said positioning.

18. The method of claim 17 further comprising adjusting said dental bracket.

* * * * *